(12) United States Patent
Chen et al.

(10) Patent No.: US 9,051,322 B2
(45) Date of Patent: Jun. 9, 2015

(54) PROCESS FOR THE PRODUCTION OF A PEMETREXED SALT

(75) Inventors: ShangHong Chen, Chiayi (TW); HuangHsiung Lin, Tainan (TW)

(73) Assignee: SCINOPHARM TAIWAN, LTD., Tainan (TW)

(*) Notice: Subject to any disclaimer, the term of this patent is extended or adjusted under 35 U.S.C. 154(b) by 330 days.

(21) Appl. No.: 13/070,114

(22) Filed: Mar. 23, 2011

(65) Prior Publication Data

US 2012/0245349 A1 Sep. 27, 2012

(51) Int. Cl.
C07D 487/04 (2006.01)
A61P 35/00 (2006.01)

(52) U.S. Cl.
CPC .................... C07D 487/04 (2013.01)

(58) Field of Classification Search
CPC .................................................. C07D 487/04
USPC ........................................................ 544/280
See application file for complete search history.

(56) References Cited

U.S. PATENT DOCUMENTS

| 5,539,113 A * | 7/1996 | Akimoto et al. ............... 544/280 |
| 2011/0124861 A1* | 5/2011 | Li et al. ............... 544/280 |
| 2013/0165654 A1* | 6/2013 | Kadaboina et al. ............ 544/280 |

FOREIGN PATENT DOCUMENTS

| EP | 0905128 A1 | 3/1999 |
| EP | 2213674 A1 | 8/2010 |
| WO | WO 99/16742 | 4/1999 |
| WO | WO 01/14379 | 3/2001 |
| WO | WO01/62760 | 8/2001 |
| WO | WO 2009143684 | * 12/2009 |
| WO | 2010/028105 A2 | 3/2010 |
| WO | WO2010/0281050 | 3/2010 |
| WO | WO 2012017443 | * 2/2012 |

OTHER PUBLICATIONS

International Search Report and Written Opinion dated May 24, 2011.
Extended European Search Report Dated Jul. 17, 2014 in connect with European related application No. 11862192.9.

* cited by examiner

*Primary Examiner* — Susanna Moore
(74) *Attorney, Agent, or Firm* — Enshan Hong; Kent H. Cheng; VLP Law Group LLP

(57) ABSTRACT

A process of making a pemetrexed salt comprising:
a) reacting a compound of formula II

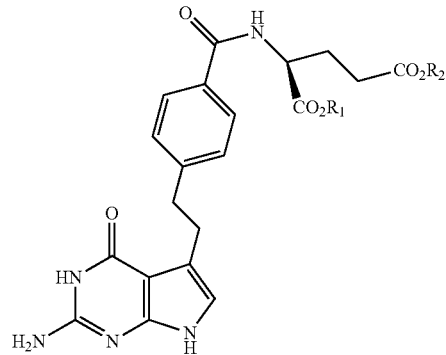

or an acid salt thereof, wherein each of $R_1$ and $R_2$ is independently a C1-C6 alkyl group, with an aqueous basic solution at a temperature of no more than 10° C. to obtain a first mixture comprising the pemetrexed salt;
b) isolating the pemetrexed salt from the first mixture.

14 Claims, No Drawings

PROCESS FOR THE PRODUCTION OF A PEMETREXED SALT

BACKGROUND OF THE INVENTION

1. Field of the Invention

The present application relates to process of making a pemetrexed salt, in particular pemetrexed disodium.

2. Description of the Related Art

Pemetrexed and salts thereof are known as anti-folate, anti-neoplastic agents. Pemetrexed's chemical name is (S)-2-[4-[2-(4-amino-2-oxo-3,5,7-triazabicyclo[4.3.0]nona-3,8,10-then-9-yl)ethyl]benzoyl]amino-pentanedioic acid and has the following chemical structure:

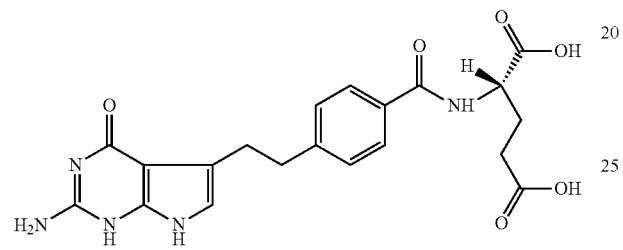

The most common salt of pemetrexed is a disodium salt, i.e., pemetrexed disodium. Pemetrexed disodium has the chemical name L-Glutamic acid, N-[4-[2-(2-amino-4,7-dihydro-4-oxo-1H-pyrrolo[2,3-d]pyrimidin-5-yl)ethyl]benzoyl]-, disodium salt. Pemetrexed disodium heptahydrate is the active ingredient of Eli Lilly and Company's ALIMTA® injectable composition. Pemetrexed disodium heptahydrate has the following chemical structure:

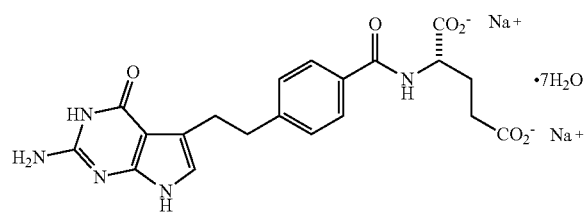

(I)

Various methods for preparing pemetrexed and pemetrexed disodium are disclosed in the art, such as International Patent Application Publication Nos. WO2001014379 and WO1999016742.

However, there is still a need for an improved process of making a pemetrexed salt.

SUMMARY OF THE INVENTION

The present application provides a process of making a pemetrexed salt comprising:

a) reacting a compound of formula II

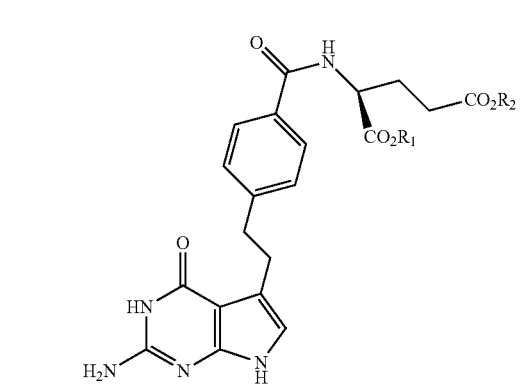

or an acid salt thereof, wherein each of $R_1$ and $R_2$ is independently a $C_1$-$C_6$ alkyl group, with an aqueous basic solution at a temperature of no more than 10° C. to obtain a first mixture comprising the pemetrexed salt;

b) isolating the pemetrexed salt from the first mixture.

The step b) may comprise:

b1) adding an organic anti-solvent to the first mixture of step a) to form a second mixture;

b2) adjusting the pH of the second mixture within a range from about 6.5 to about 9.5 to form a third mixture;

b3) separating the pemetrexed salt from the third mixture.

The steps b1)-b2) may be conducted at no more than 10° C., more preferably no more than 5° C.

Preferably, the step a) is conducted at no more than 5° C.

The organic anti-solvent may be any suitable organic solvent, preferably a water miscible solvent, more preferably a solvent selected from isopropanol, propanol, acetone, methanol, ethanol, acetonitrile, THF, and combinations thereof.

The acid salt of the compound of formula (II) may be any suitable salt with at least one counter anion. For example, the acid salt may be selected from p-TSA (p-toluenesulfonic acid), sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, benzensulfonic, methanesulfonic, trifluoroacetic, hippuric salts, and combinations thereof. Preferably, the acid salt is a p-TSA salt.

Each of $R_1$ and $R_2$ in formula (II) is preferably an ethyl group.

The aqueous basic solution is preferably sodium hydroxide solution.

The pemetrexed salt is preferably pemetrexed disodium.

The crude pemetrexed disodium obtained in accordance with the above-described process may be further recrystallized, preferably at a temperature of 15 to 30° C., more preferably at a temperature of 20-25° C.

In step b), the pH of the resulting solution is preferably adjusted to from about 7.5 to about 8.5. The pH discussed in the step b) is preferably adjusted by a pH adjusting solution, e.g., hydrochloric acid in a suitable solvent, preferably a water miscible solvent, more preferably a solvent selected from isopropanol, propanol, water, acetonitrile, methanol, ethanol, THF, and acetone, more preferably a pH adjusting aqueous solution.

The various features of novelty which characterize the invention are pointed out with particularity in the claims annexed to and forming a part of the disclosure. For a better understanding of the invention, its operating advantages, and specific objects attained by its use, reference should be had to the descriptive matter in which there are illustrated and described preferred embodiments of the invention.

DETAILED DESCRIPTION OF THE PRESENTLY PREFERRED EMBODIMENTS

The following embodiments are provided to further explain, but not to limit, the present invention.

As discussed above, the pemetrexed salt is formed from the reaction between compound of formula (II) and the basic aqueous solution. For example, the pemetrexed salt may be di-sodium salt, potassium salt, lithium salt, or calcium salt.

The present application discloses a method for the preparation of crude pemetrexed disodium, which may be further purified to pemetrexed disodium 2.5 $H_2O$ crystalline form. In accordance with an embodiment of the present invention, the aforesaid preparation method may comprise a hydrolysis step of formula (II) to furnish crude pemetrexed disodium at a low temperature followed by the addition of IPA and then the pH is adjusted by adding hydrochloric acid.

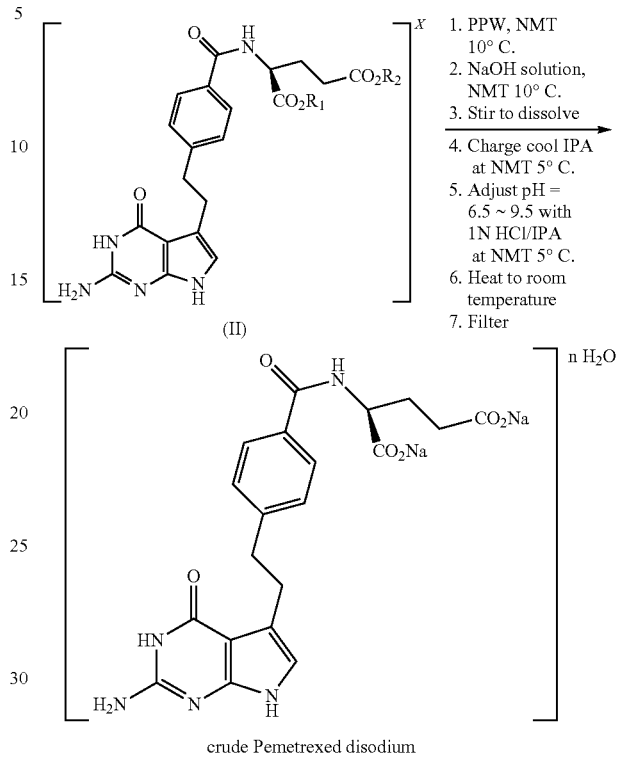

In the above Formula (II), each of $R_1$ and $R_2$ is independently a C1-C6 alkyl group, such as ethyl, X is a counter anion so that the compound of formula (II) is an acid salt, such as a p-TSA salt, n represents the number of water, which typically ranges from 2.5 to 7.0.

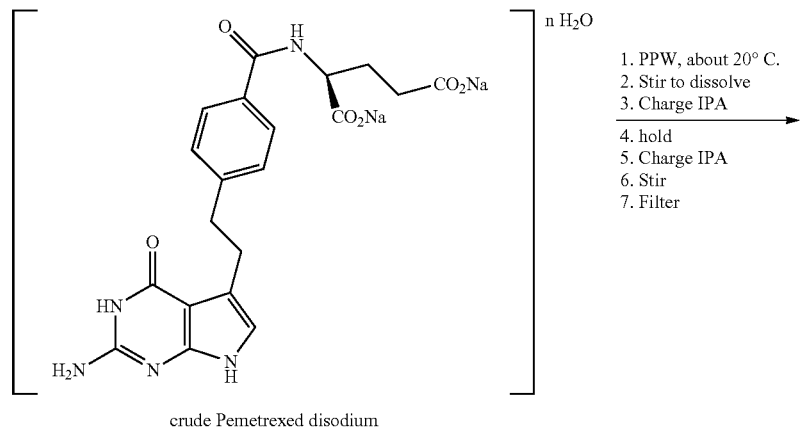

crude Pemetrexed disodium

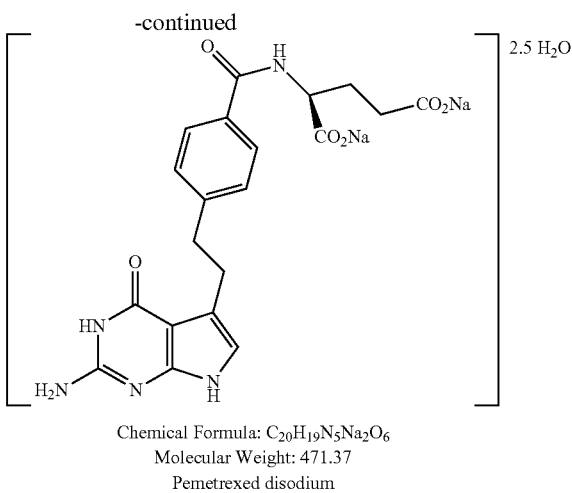

Chemical Formula: $C_{20}H_{19}N_5Na_2O_6$
Molecular Weight: 471.37
Pemetrexed disodium In comparison with the prior art, the embodiments of the present invention have the following advantages:

1) The reaction of the compound of formula (II) or salt thereof with an aqueous basic solution is preferably conducted at a low temperature, e.g., no more than 10° C., in comparison with the room temperature of WO2001014379 and WO1999016742. As shown in Table 1 shown below, the inventors of the present invention unexpectedly discovered that impurities can be reduced or minimized by conducting the reaction at a low temperature. As noted above, after the reaction step, the low temperature is preferably maintained during the steps of adjusting pH and adding anti-solvent.

2) The anti-solvent is preferably added before adjusting the pH value. The inventors unexpectedly discovered that by doing so, the mixture can be diluted by the addition of the anti-solvent before the adjusting step, therefore minimizing local heat effect and formation of impurities. In comparison, WO2001014379 discloses adjusting the pH value before the addition of an anti-solvent.

3) In accordance with the present invention, the compound of formula (II) can be converted to a pemetrexed salt (e.g., at a pH of 6.5 to 9.5). In contrast, the process of WO1999016472 comprises making pemetrexed free form first (at a pH of about 3), and then converting the free form to a salt (at a pH of about 6.5 to 9.5). The process of the present invention is simpler and more convenient.

4) In accordance with an embodiment of the present invention, the crude pemetrexed salt may be crystallized at a room temperature; whereas in accordance with WO2001014379, the crystallizing is conducted at about 70° C. The cooling, heating, and adjusting pH steps of WO2001014379 may be avoided in accordance with the embodiment of the present invention. The process of the present invention can save workup procedures and has better control of impurity.

TABLE 1

The stability of pemetrexed disodium in sodium hydroxide at different temperature

| Rex. Temperature (° C.) | 1 hr* (%) | 2 hr* (%) | 4 h* (%) | 6 hr* (%) |
|---|---|---|---|---|
| 5 | 0.012 | 0.013 | 0.035 | 0.066 |
| 10 | 0.051 | 0.053 | 0.070 | 0.075 |
| 15 | 0.076 | 0.085 | 0.110 | 0.123 |

*The content of impurity based on HPLC spectra's % Area.

Example 1

Preparation of Crude Pemetrexed Disodium

N-[4-2-(2-Amino-4,7-dihydro-4-oxo-1H-pyrrolo[2,3-d]pyrimidin-5-yl)ethyl]benzoyl]-L-glutamic Acid Diethyl Ester 4-Methylbenzenesulfonic Acid Salt and purified process water (PPW) (about 10 kg) are charged to a suitable vessel under nitrogen. The reactor is cooled to NMT 10° C. under nitrogen. Pre-cooled sodium hydroxide solution (about 1.5 kg)/PPW (about 11.4 kg) are added and the temperature is maintained at NMT 10° C. The mixture is stirred at NMT 10° C. until the solid is dissolved. Pre-cooled isopropanol (about 62.8 kg) is added and the mixture temperature is maintained at NMT 5° C. Pre-cooled 1 N hydrochloric acid in isopropanol is added to adjust the pH to 6.5 to 9.5, preferably between pH 7.5 to pH 8.5, at NMT 5° C. The mixture is warmed to a room temperature (i.e., 15-30° C., preferably 20-25° C.) and stirred. The solids are filtered and washed with isopropanol/PPW. The wet cake is vacuum dried to provide crude pemetrexed disodium (about 2.30 kg).

Example 2

Purification of Crude Pemetrexed Disodium to Pemetrexed Disodium

Crude pemetrexed disodium (about 2.1 kg) and PPW (about 23.3 kg) are charged under nitrogen to a suitable vessel at 15 to 30° C. Isopropanol (about 28.3 kg) is added slowly to cloud point and stirred. Isopropanol (up to about 55 kg) is charged and stirred. The solids are filtered and washed with isopropanol/PPW. The wet cake is vacuum dried to provide pemetrexed disodium (about 1.9 kg) (90% Yield). 1H NMR ($D_2O$): δ 7.51 (2H, d, J=8.0 Hz), 6.98 (2H, d, J=8.0 Hz), 6.12 (1H, s), 4.26-4.23 (H, m), 3.60-3.54 (4H, m), 2.27-2.23 (2H, m), 2.13-2.08 (1H, m), 2.00-1.94 (1H, m)

What is claimed is:

1. A process of making a pemetrexed salt comprising:
   a) reacting a compound of formula II

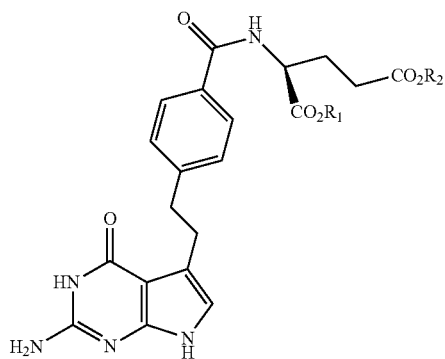

or an acid salt thereof, wherein each of $R_1$ and $R_2$ is independently a C1-C6 alkyl group, with an aqueous basic solution at a temperature of no more than 10° C. to directly obtain a first mixture comprising the pemetrexed salt, wherein the reaction mixture is a solution;
   b1) adding an organic anti-solvent to the first mixture of step a) to form a second mixture;
   b2) adjusting the pH of the second mixture within a range from about 6.5 to about 9.5 to form a third mixture; and
   b3) separating the pemetrexed salt from the third mixture.

2. The process of claim 1 wherein the steps b1)-b2) are conducted at no more than 10° C.

3. The process of claim 1 wherein the steps b1)-b2) are conducted at no more than 5° C.

4. The process of claim 1 wherein the step a) is conducted at no more than 5° C.

5. The process of claim 1 wherein the organic anti-solvent is selected from isopropanol, propanol, acetone, methanol, ethanol, acetonitrile, THF, and combinations thereof.

6. The process of claim 1 wherein the acid salt is selected from p-TSA, sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, benzensulfonic, methanesulfonic, trifluoroacetic, hippuric salts or combinations thereof.

7. The process of claim 1 wherein a p-TSA salt of the compound of formula (II) is used in the reacting step.

8. The process of claim 1 wherein each of $R_1$ and $R_2$ is an ethyl group.

9. The process of claim 1 wherein the aqueous basic solution is sodium hydroxide solution.

10. The process of claim 1 wherein the pemetrexed salt is pemetrexed disodium.

11. The process of claim 1 further comprising a step of recrystallizing the pemetrexed salt isolated from the step b3) at a temperature of 15 to 30° C.

12. The process of claim 11 wherein the recrystallizing is conducted in water and an organic anti-solvent.

13. A process for preparing a compound of formula (III)

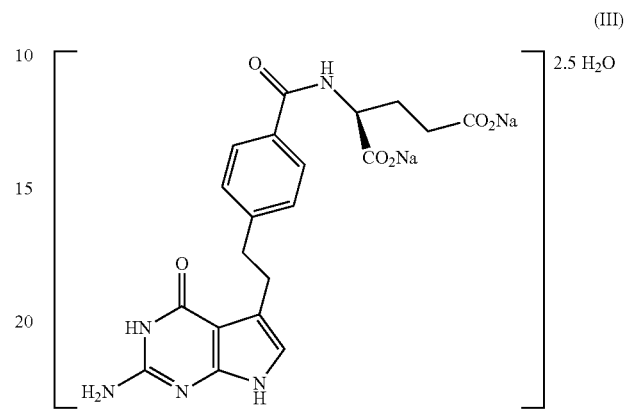

comprising the steps of:
   a) reacting a compound of formula (II'):

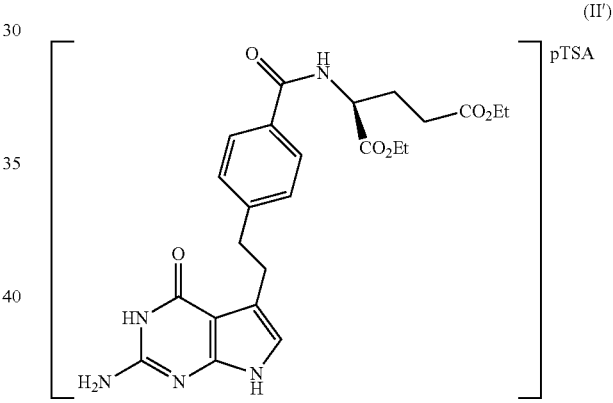

with an aqueous basic solution to obtain a first mixture, which is a solution;
   b) adding an organic anti-solvent to the first mixture to form a second mixture;
   c) adjusting the pH of the second mixture within a range from about 6.5 to about 9.5 to form a third mixture; and
   d) warming the third mixture to a room temperature and then filtering.

14. The process of claim 13, wherein the steps a)-c) are conducted at no more than 10° C.

* * * * *